(12) United States Patent
Hori

(10) Patent No.: US 10,206,640 B2
(45) Date of Patent: Feb. 19, 2019

(54) X-RAY COMPUTED TOMOGRAPHY IMAGING APPARATUS AND GANTRY APPARATUS

(71) Applicant: Toshiba Medical Systems Corporation, Otawara-shi (JP)

(72) Inventor: Hiroshi Hori, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 198 days.

(21) Appl. No.: 15/278,314

(22) Filed: Sep. 28, 2016

(65) Prior Publication Data
US 2017/0105689 A1    Apr. 20, 2017

(30) Foreign Application Priority Data

Oct. 16, 2015 (JP) ................ 2015-204643
Sep. 14, 2016 (JP) ................ 2016-179447

(51) Int. Cl.
*A61B 6/00* (2006.01)
*A61B 6/03* (2006.01)

(52) U.S. Cl.
CPC ........... *A61B 6/4435* (2013.01); *A61B 6/032* (2013.01); *A61B 6/54* (2013.01)

(58) Field of Classification Search
CPC .......... A61B 6/4435; A61B 6/032; A61B 6/54

USPC ....................... 378/4–20, 193–200
See application file for complete search history.

(56) References Cited

U.S. PATENT DOCUMENTS

| | | | |
|---|---|---|---|
| 2004/0228450 A1 | 11/2004 | Mueller | |
| 2007/0274437 A1* | 11/2007 | Schindler | A61B 6/035 378/20 |
| 2011/0228910 A1* | 9/2011 | Gregerson | A61B 6/4488 378/200 |
| 2012/0140883 A1 | 6/2012 | Iwakiri et al. | |

FOREIGN PATENT DOCUMENTS

| | | |
|---|---|---|
| JP | 2004-237103 | 8/2004 |
| JP | 2012-120651 | 6/2012 |
| JP | 2013-9819 | 1/2013 |

* cited by examiner

*Primary Examiner* — Courtney D Thomas
(74) *Attorney, Agent, or Firm* — Oblon, McClelland, Maier & Neustadt, L.L.P.

(57) ABSTRACT

According to one embodiment, an X ray computed tomography imaging apparatus includes a gantry and a column. The gantry includes a first gantry intake port, and a second gantry intake port. The first gantry intake port draws air in the first state. The second gantry intake port draws air in the second state. The column includes a first column exhaust port and a second column exhaust port. The first column exhaust port communicates with the first gantry intake port in the first state. The second column exhaust port communicates with the second gantry intake port in the second state.

20 Claims, 11 Drawing Sheets

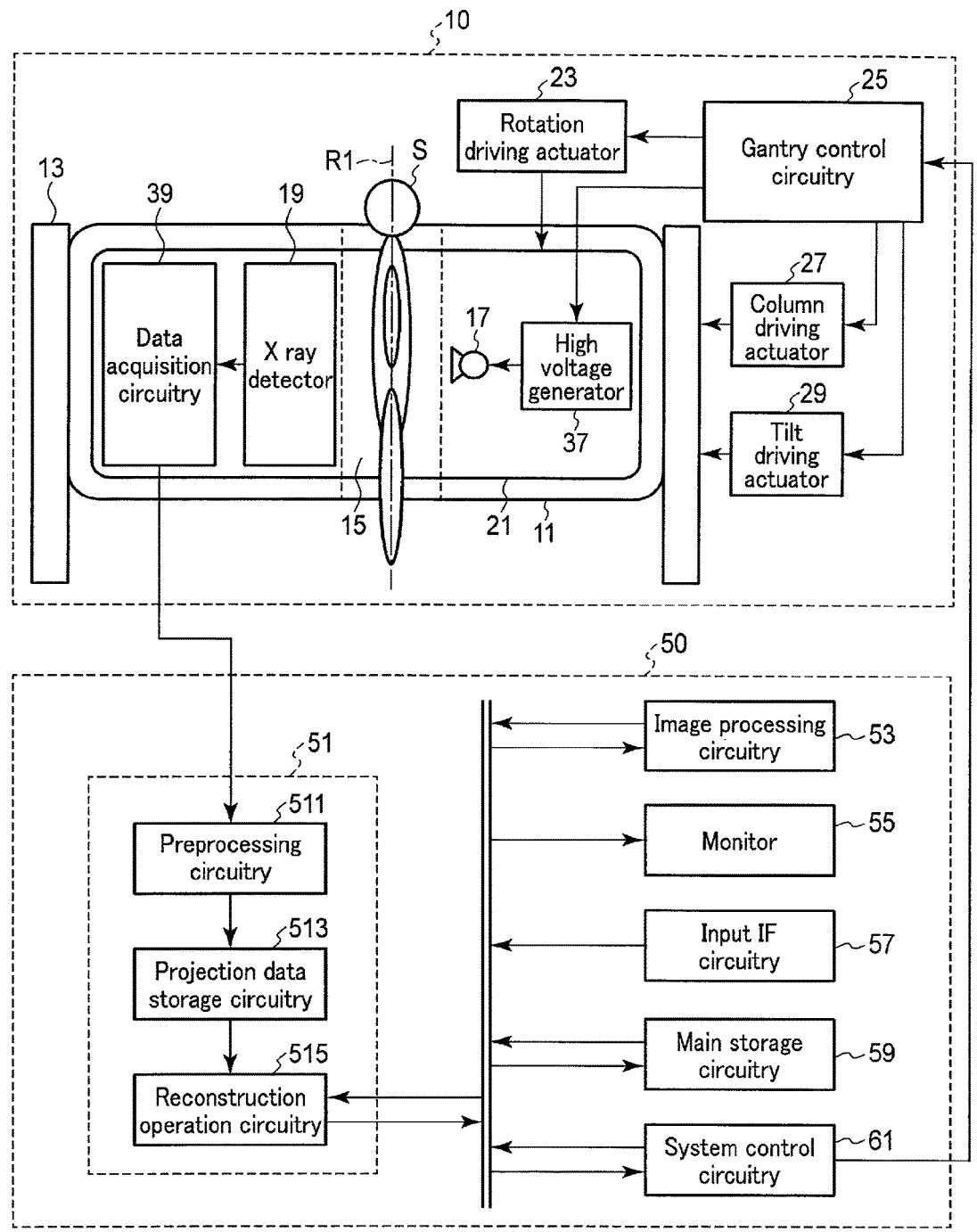
F I G. 1

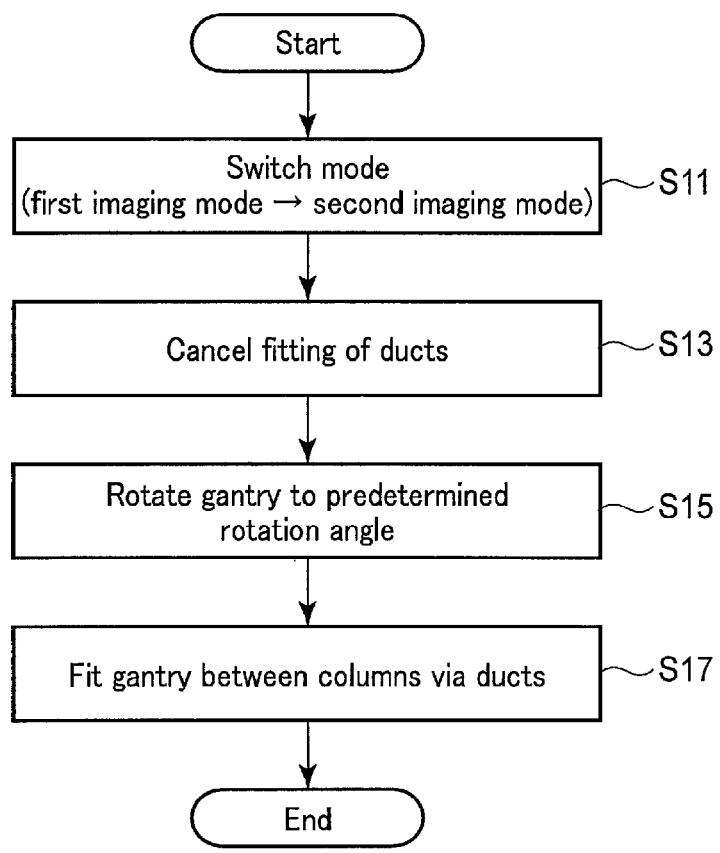
F I G. 6

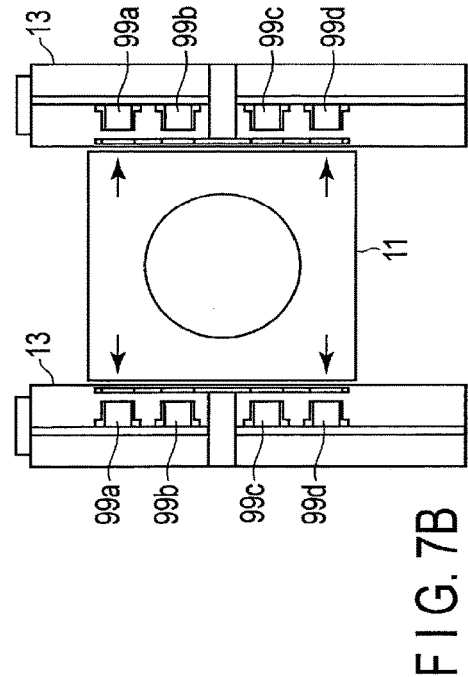
F I G. 7B
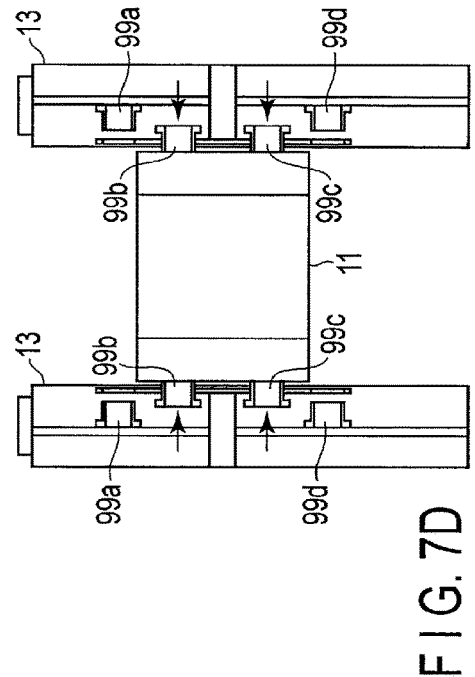
F I G. 7D
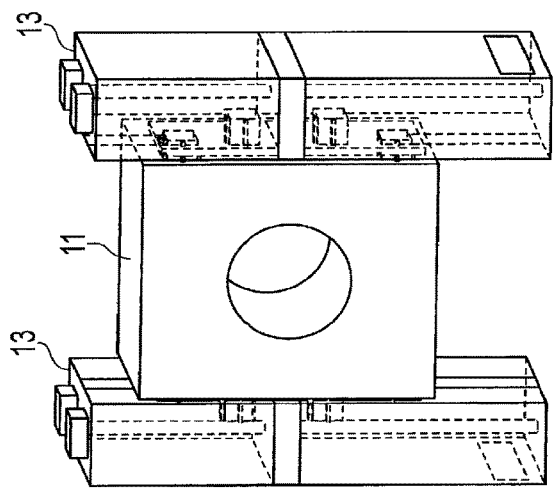
F I G. 7A
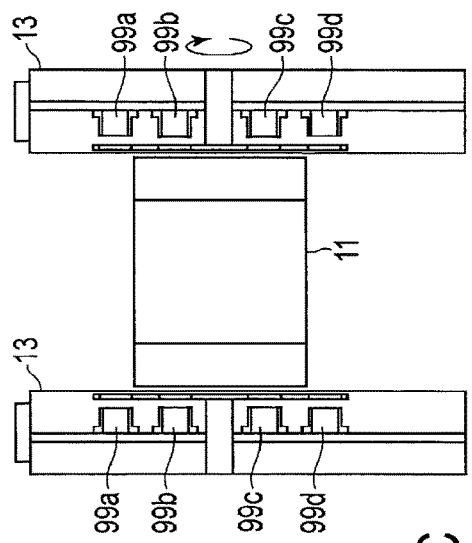
F I G. 7C

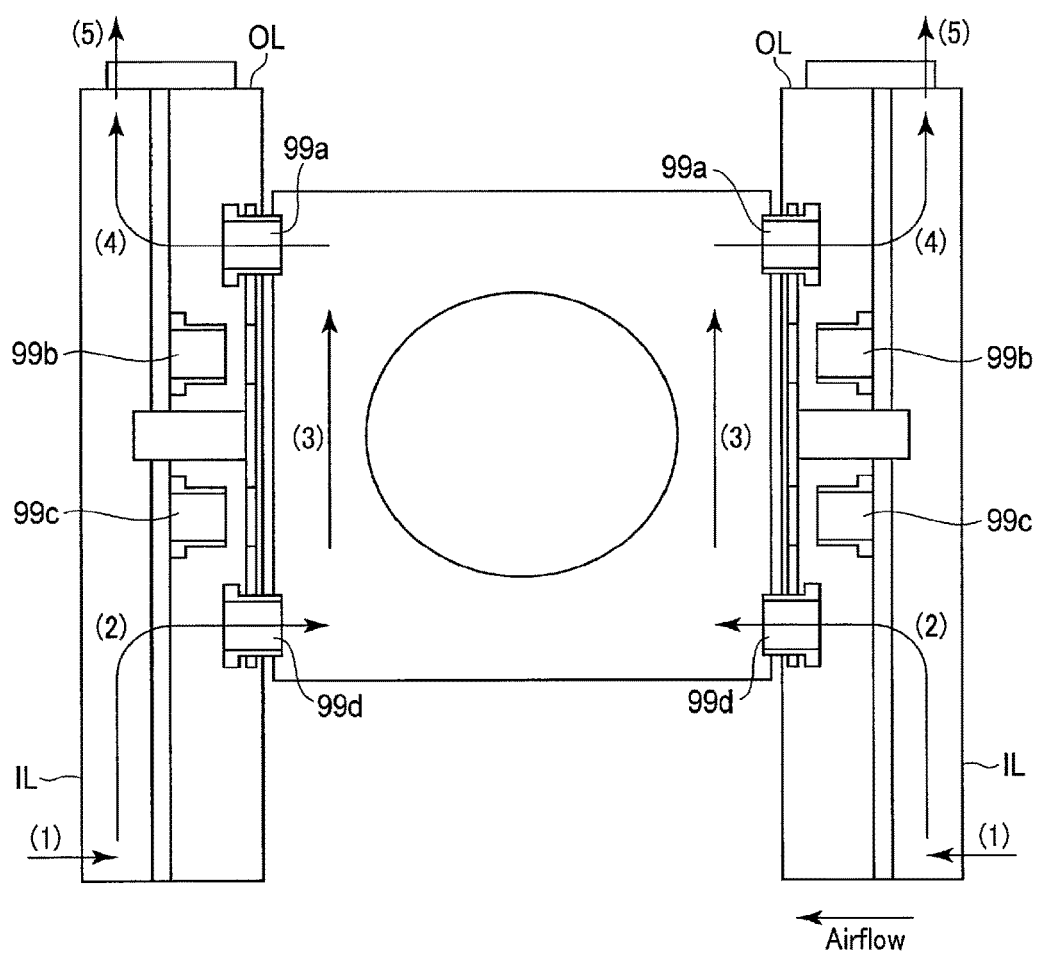
F I G. 10

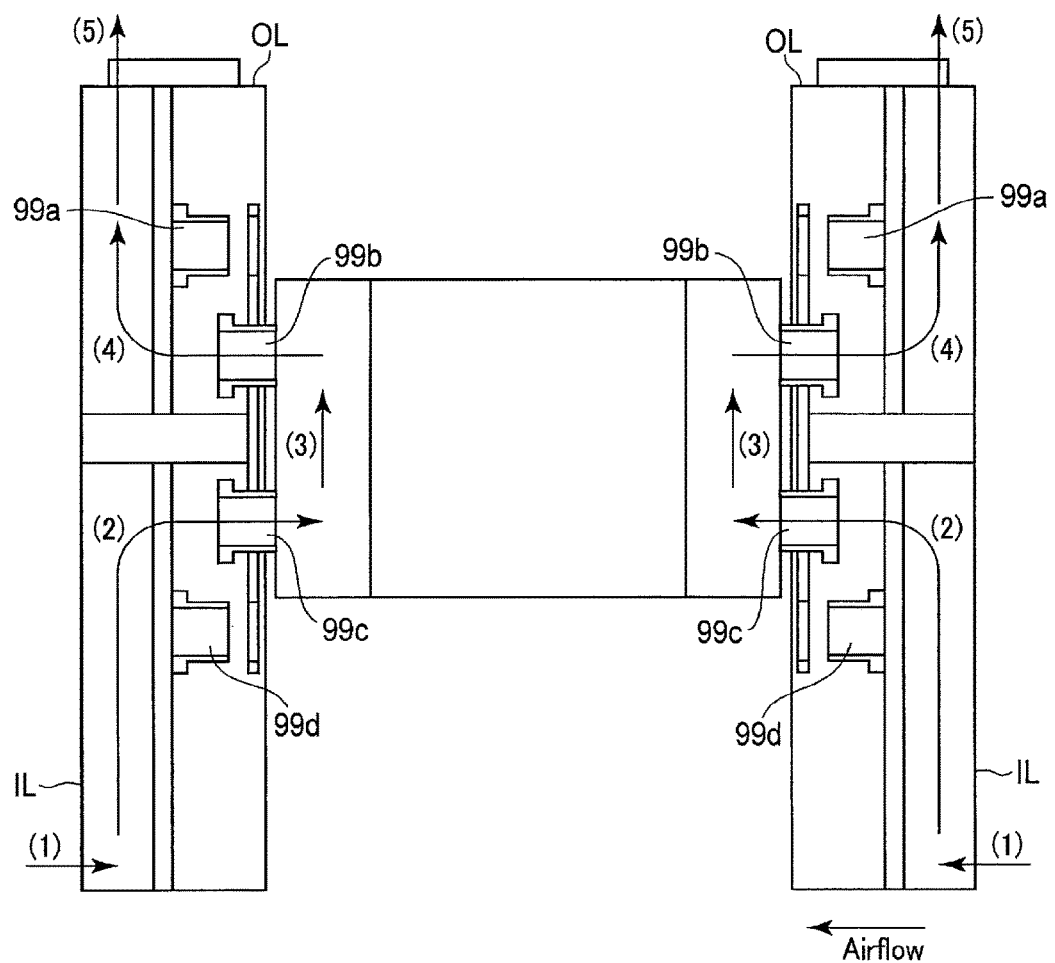
F I G. 11

X-RAY COMPUTED TOMOGRAPHY IMAGING APPARATUS AND GANTRY APPARATUS

CROSS-REFERENCE TO RELATED APPLICATIONS

This application is based upon and claims the benefit of priority from Japanese Patent Application No. 2015-204643, filed Oct. 16, 2015, and No. 2016-179447, filed Sep. 14, 2016, the entire contents of which are incorporated herein by reference.

FIELD

Embodiments described herein relate generally to an X-ray computed tomography imaging apparatus and a gantry apparatus.

BACKGROUND

X-ray CT (Computed Tomography) imaging is normally executed in a lying state in which a subject lies on a bed. For this reason, a heat exhaust mechanism provided in the X-ray CT apparatus that executes X-ray CT imaging in the lying state draws, for example, air from the lower portion of the gantry and exhaust the air that has risen inside the gantry from the upper portion of the gantry.

However, when implementing an X-ray CT apparatus (an X-ray CT apparatus also used for standing position imaging) capable of executing imaging in the lying state and recently demanded imaging in standing and sitting states by itself, the direction of the bore of the gantry changes by 90° between the imaging in the lying state and the imaging in the standing and sitting states. For this reason, when the heat exhaust mechanism is provided in the gantry as described above, air is drawn from a side surface and exhausted from a side surface at the time of imaging in the standing or sitting state. That is, the heat exhaust efficiency lowers in the imaging in the standing and sitting states as compared to the imaging in the lying state. In addition, the air is exhausted from the side surface and, for example, a blast of hot air strikes the subject and the operator. This is undesirable from the viewpoint of hygiene. Furthermore, noise generated by air drawing and exhaust is unpleasant for the subject and the operator.

BRIEF DESCRIPTION OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing an X-ray CT apparatus according to the embodiment;
FIG. 6 is a flowchart showing the procedure of a switching operation from a first imaging mode to a second imaging mode in the X-ray CT apparatus according to the embodiment;
FIG. 7A is a view for explaining the procedure of the switching operation from the first imaging mode to the second imaging mode in the X-ray CT apparatus according to the embodiment;
FIG. 7B is a view for explaining the procedure of the switching operation from the first imaging mode to the second imaging mode in the X-ray CT apparatus according to the embodiment;
FIG. 7C is a view for explaining the procedure of the switching operation from the first imaging mode to the second imaging mode in the X-ray CT apparatus according to the embodiment;
FIG. 7D is a view for explaining the procedure of the switching operation from the first imaging mode to the second imaging mode in the X-ray CT apparatus according to the embodiment;
FIG. 10 is a view showing a heat exhaust path in the X-ray CT apparatus according to the embodiment when executing lying position imaging;
and
FIG. 11 is a view showing a heat exhaust path in the X-ray CT apparatus according to the embodiment when executing standing or sitting position imaging.

DETAILED DESCRIPTION

Figure 2B:
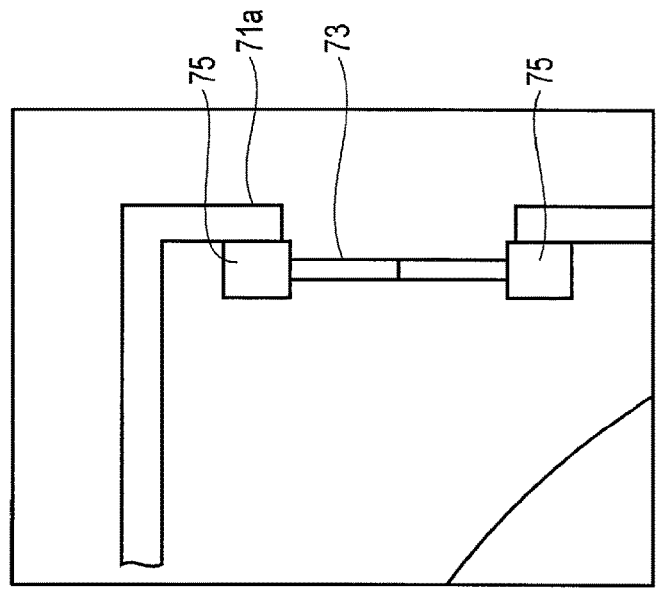
FIG. 2B is a view showing the structure of the side surface of the gantry shown in FIG. 1.

In general, according to one embodiment, an X-ray computed tomography imaging apparatus includes a gantry, and a column. The gantry configured to hold an X-ray source configured to generate X-rays and an X-ray detector configured to detect the X-rays. The column capable of supporting the gantry in a first state in which a center axis of a bore of the gantry is perpendicular to a floor surface of an examination room and in a second state in which the center axis of the bore is parallel to the floor surface of the examination room. The gantry includes a first gantry intake port, and a second gantry intake port. The first gantry intake port configured to draw air in the first state. The second gantry intake port configured to draw air in the second state. The column includes a first column exhaust port, and a second column exhaust port. The first column exhaust port capable of communicating with the first gantry intake port in the first state. The second column exhaust port capable of communicating with the second gantry intake port in the second state.

An X-ray computed tomography imaging apparatus according to the embodiment will now be described with reference to the accompanying drawing. Note that the same reference numerals denote constituent elements having almost the same functions and arrangements in the following explanation, and a repetitive description thereof will be made only when necessary.

FIG. 1 is a block diagram showing an X-ray computed tomography imaging apparatus according to this embodiment.

As shown in FIG. 1, an X-ray computed tomography imaging apparatus (to be referred to as an X-ray CT apparatus hereinafter) according to this embodiment includes a gantry apparatus 10 and a console 50. For example, the gantry apparatus 10 is placed in a CT examination room, and the console 50 is placed in a control room adjacent to the CT examination room. The gantry apparatus 10 and the console 50 are connected wirelessly or via a cable to be communicable with each other. The gantry apparatus 10 is a scanning apparatus having an arrangement for performing X-ray computed tomography imaging of a subject S in a standing or sitting position. The console 50 is a computer that controls the gantry apparatus 10.

As shown in FIG. 1, a gantry 11 is an almost cylindrical structure with a bore 15 that forms a field of view. As shown in FIG. 1, the gantry 11 stores an X-ray tube 17 and an X-ray detector 19 which are arranged to face each other across the bore 15.

More specifically, the gantry 11 further includes a main frame (not shown) made of a metal such as aluminum, and a rotation frame 21 supported by the main frame via a bearing and the like to be rotatable about a center axis R1. An annular electrode (not shown) is provided on the contact portion of the main frame to the rotation frame 21. A conductive sliding element (not shown) is attached to the contact portion of the main frame to be in slidable contact with the annular electrode. The rotation frame 21 is a metal frame formed into a ring shape by a metal such as aluminum, to which, for example, the X-ray tube 17 and the X-ray detector 19 are attached. The X-ray tube 17 and the X-ray detector 19 may be, for example, fitted in concave portions formed in the rotation frame 21 or fastened using fasteners such as a screw.

Figure 2A:
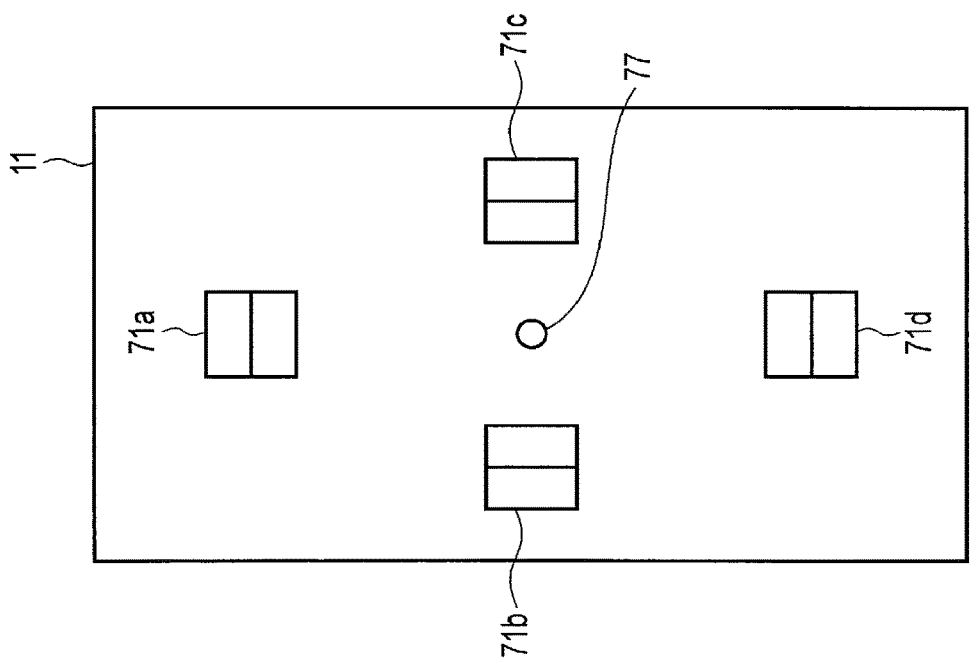
FIG. 2A is a view showing the structure of a side surface of a gantry shown in FIG. 1.

FIGS. 2A and 2B are views showing the structure of a side surface of the gantry 11 shown in FIG. 1. As shown in FIG. 2A, the gantry 11 includes vent holes 71*a*, 71*b*, 71*c*, and 71*d* in the side surface. As shown in FIG. 2B, lids 73 are provided on each of the vent holes 71*a*, 71*b*, 71*c*, and 71*d*. The lids 73 are supported to open/close about support members 75. Note that the support member 75 includes, for example, a spring, a hinge, and the like. The gantry 11 is connected to columns 13 such that the center axis R1 can rotate about a horizontal axis (to be referred to as a tilt axis hereinafter) parallel to the floor surface. At this time, the gantry 11 is connected to the columns 13 via bearings 77 and the like.

The rotation frame 21 rotates about the center axis R1 at a predetermined angular velocity upon receiving power from a rotation driving actuator 23. The rotation driving actuator 23 generates the power to rotate the rotation frame 21 under the control of gantry control circuitry 25. The rotation driving actuator 23 drives at a rotation speed corresponding to the duty ratio or the like of a driving signal from the gantry control circuitry 25, thereby generating the power. The rotation driving actuator 23 is implemented by, for example, a motor such as a direct drive motor or a servo motor. The rotation driving actuator 23 is stored in, for example, the gantry 11.

The column 13 is a base that supports the gantry 11 away from the floor surface (placement surface). The column 13 has, for example, a columnar shape such as a circular prismatic shape or a prismatic shape. The column 13 is made of, for example, an arbitrary substance such as a plastic or a metal. The column 13 is attached to, for example, a side surface of the gantry 11. To perform X-ray computed tomography imaging of the subject S in the standing or sitting position, the columns 13 slidably support the gantry 11 in a state in which the center axis R1 of the bore 15 is kept perpendicular to the floor surface.

The column 13 stores a driving actuator (to be referred to as a column driving actuator 27 hereinafter) for sliding of the gantry 11 in the vertical direction. The column driving actuator 27 generates power to slide the gantry 11 in the vertical direction under the control of the gantry control circuitry 25. More specifically, the column driving motor 27 drives at a rotation speed corresponding to the duty ratio or the like of a driving signal from the gantry control circuitry 25, thereby generating the power. The column 13 slides the gantry 11 in the vertical direction with respect to the column 13 upon receiving the power from the column driving actuator 27. The column driving actuator 27 is implemented by, for example, a motor such as a direct drive motor or a servo motor.

The column 13 supports, for example, the gantry 11 rotatably about the tilt axis. In this case, the column 13 and the gantry 11 are connected via the bearing 77 and the like such that the gantry 11 can rotate about the tilt axis.

The column 13 stores a driving actuator (to be referred to as a tilt driving actuator 29 hereinafter) for tilt of the gantry 11 about the tilt axis. The tilt driving actuator 29 generates power to tilt the gantry 11 about the tilt axis under the control of the gantry control circuitry 25. More specifically, the tilt driving actuator 29 drives at a rotation speed corresponding to the duty ratio or the like of a driving signal from the gantry control circuitry 25, thereby generating the power. The column 13 tilts the gantry 11 about the tilt axis upon receiving the power from the tilt driving actuator 29. The tilt driving actuator 29 is implemented by, for example, a motor such as a direct drive motor or a servo motor.

This allows the single gantry apparatus 10 to selectively execute lying position imaging and standing and sitting position imaging.

The columns 13 are provided on both sides of the gantry 11. However, the embodiment is not limited to this. For example, one column 13 may be connected to only one of the both sides of the gantry 11. The column 13 has a columnar shape. However, the embodiment is not limited to this. For example, the column 13 may have any shape such as a U shape as long as it can support at least one side portion of the gantry 11.

FIGS. 3A to 3D are views showing the internal structure of the column 13 shown in FIG. 1. Note that the interior of the column 13 is not illustrated. Although FIG. 3 illustrates only one column 13, the other column 13 also has the same structure.

Figure 3D:
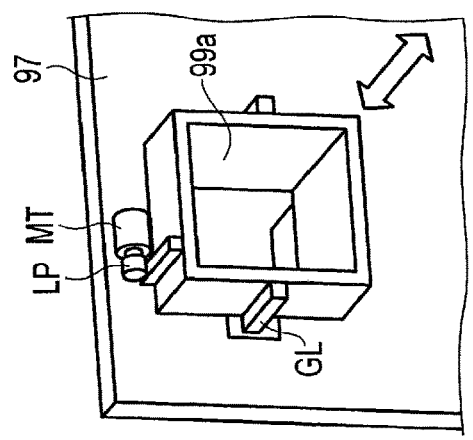
FIG. 3D is a view showing the internal structure of the column shown in FIG. 1.
Figure 3C:
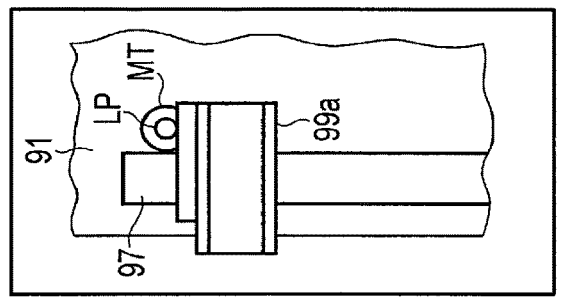
FIG. 3C is a view showing the internal structure of the column shown in FIG. 1.
Figure 3B:
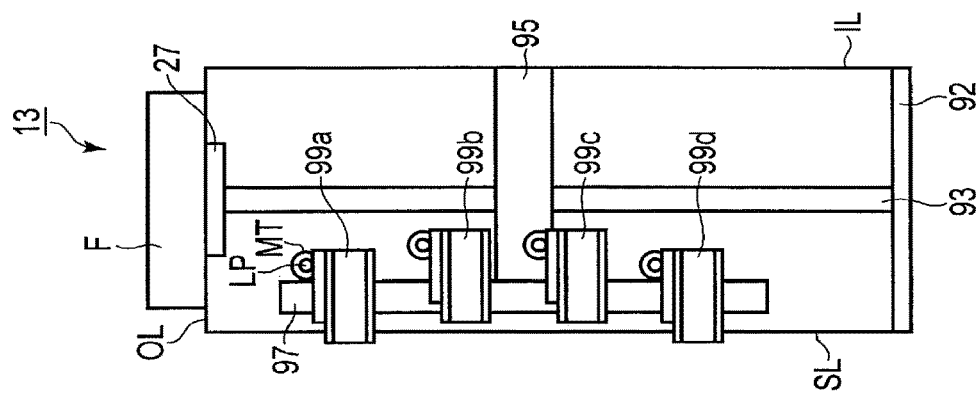
FIG. 3B is a view showing the internal structure of the column shown in FIG. 1.
Figure 3A:
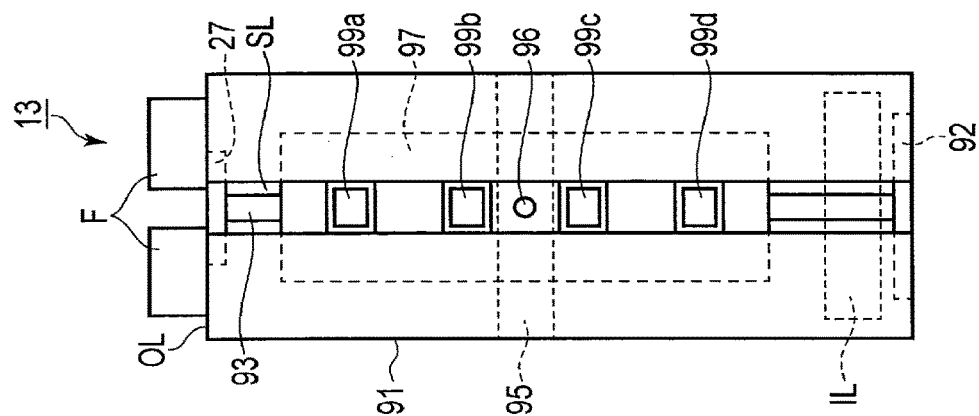
FIG. 3A is a view showing the internal structure of a column shown in FIG. 1.

As shown in FIG. 3A, the housing (to be referred to as a column housing 91 hereinafter) of the column 13 stores a slide actuator slides the gantry 11 in the vertical direction with respect to the placement surface. The slide actuator is implemented by, for example, a ball screw and a slider. That is, the slide actuator is implemented by a screw shaft 93, a slider 95, and an arm 97.

The screw shaft 93 is a member moves the slider 95 and the arm 97 joined to the slider 95 in the vertical direction by the rotation of its own. The screw shaft 93 is placed in the column housing 91 such that its axis becomes parallel to the vertical direction. That is, the screw shaft 93 is placed by arranging its axis along the longitudinal direction of the column housing 91. One end of the screw shaft 93 is rotatably supported by a support 92.

The support 92 is a member places the screw shaft 93 in the column housing 91. The support 92 is provided, for example, at one end of the column housing 91. The other end of the screw shaft 93 is connected to the column driving actuator 27. The column driving actuator 27 is implemented by, for example, a motor and the like. The column driving actuator 27 is provided at the other end facing the support 92 in the column housing 91. For example, as shown in FIG. 3B, the support 92 may be provided in the upper portion of the column housing 91, and the column driving actuator 27 may be provided in the lower portion of the column housing 91. However, the positional relationship between the support 92 and the column driving actuator 27 is not limited to the above example. For example, the support 92 may be provided in the lower portion of the column housing 91, and the column driving actuator 27 may be provided in the upper portion of the column housing 91.

The slider 95 is a member that moves in the vertical direction in synchronism with the rotation of the screw shaft 93. The slider 95 has a through hole with a thread groove (female screw) threadably engaging with the thread groove (male screw) of the screw shaft 93. The slider 95 is screwed on the screw shaft 93. The screw shaft 93 rotates in synchronism with the rotation of the rotation shaft of the column driving actuator 27. The slider 95 slides along the axial direction (that is, the vertical direction) of the screw shaft 93 along with the rotation of the screw shaft 93. The slider 95 also serves as a partition, and separates the internal space of the column housing 91 into an upper portion and a lower portion. This forms a structure that prevents air drawn into the gantry 11 and air exhausted from the gantry 11 from mixing.

The arm 97 is a member joined to the slider 95 and moves the gantry 11 in the vertical direction in synchronism with the vertical movement of the slider 95. A tilt actuator connects the gantry 11 to the column housing 91 such that the gantry 11 can rotate about the tilt axis is attached to the arm 97. The tilt actuator is implemented by, for example, a bearing 96.

The bearing 96 is a member connects the gantry 11 to the column housing 91 such that the gantry 11 can rotate about the tilt axis. The bearing 96 is provided in the arm 97 such that the axis matches the tilt axis. A shaft member provided in the bearing 96 may directly be attached to the arm 97 by a fastener or the like or attached via an existing mechanical element. One end of the shaft member is connected to the tilt driving actuator 29. The tilt driving actuator 29 is provided in, for example, the slider 95. The shaft member rotates in synchronism with the rotation of the rotation shaft of the tilt driving actuator 29. The tilt driving actuator 29 and the bearing 96 are directly connected. However, the embodiment is not limited to this. For example, the tilt driving actuator 29 and the bearing 96 may indirectly be connected via a mechanical element such as a gear. The tilt driving actuator 29 is provided in the slider 95. However, the embodiment is not limited to this. The tilt driving actuator 29 may be provided in any place of the column housing 91 as long as it is directly or indirectly connected to the shaft member.

The column housing 91 is provided with a slit SL (shown in FIG. 3A) along the vertical direction so that the slider 95 can slide in the vertical direction in synchronism with the rotation of the rotation shaft of the column driving actuator 27. This allows the bearing 96 and ducts 99a, 99b, 99c, and 99d to slide in the vertical direction in synchronism with the rotation of the rotation shaft of the column driving actuator 27 without mechanical interference of the column housing 91 or the like. The slit SL is covered with, for example, a rubber plate, a brush, or the like. This forms a structure that hardly leaks air from the slit SL.

As shown in FIG. 3E, the arm 97 is provided with the ducts 99a, 99b, 99c, and 99d (including vent holes). Each of the ducts 99a, 99b, 99c, and 99d includes a duct driving actuator configured to extract/insert the duct in the direction of an arrow shown in FIG. 3C and FIG. 3D. The duct driving actuator is implemented by, for example, a motor MT, a rack and pinion LP, and guiderails GL. Each of the ducts 99a, 99b, 99c, and 99d is supported in the arm 97 by the guiderails GL. The ducts 99a, 99b, 99c, and 99d are extracted/inserted from/into the slit SL along the guiderails GL. The ducts 99a, 99b, 99c, and 99d are extracted/inserted from/into the slit SL by controlling driving of the motor MT by the gantry control circuitry 25.

The column 13 includes, in the lower portion of the column housing 91, an intake port IL draws external air into the column housing 91. The intake port IL is provided, for example, in a side surface on the opposite side of the side surface that supports the gantry 11. The column 13 includes, in the upper portion of the column housing 91, an exhaust port OL exhausts internal air out of the column housing 91. Note that the position of the intake port IL and the position of the exhaust port OL shown in FIG. 3A are merely examples. The intake port IL and the exhaust port OL can be located at any position as long as they can draw and exhaust air at positions apart from the subject S and the operator in consideration of noise and the like.

As shown in FIG. 3B, for example, the exhaust port OL is provided with exhaust fans F that exhaust internal air out of the column housing 91. In addition, the intake port IL may be provided with an intake fan that draws external air into the column housing 91.

An intake duct that makes the intake port IL communicate with the vent hole of the duct 99c or the vent hole of the duct 99d may be provided. An exhaust duct that makes the vent hole of the duct 99a or the vent hole of the duct 99b communicate with the exhaust port OL may be provided. When the intake duct is provided, air does not leak from the slit SL in a fluid path from the intake port to the vent hole of the duct 99c or the vent hole of the duct 99d. When the exhaust duct is provided, air does not leak from the slit SL in a fluid path from the vent hole of the duct 99a or the vent hole of the duct 99b to the exhaust port OL. That is, a rubber plate, a brush, or the like that covers the slit SL is unnecessary.

The X-ray tube 17 generates X-rays upon receiving a high voltage applied from a high voltage generator 37. The high voltage generator 37 is attached to, for example, the rotation frame 21. Under the control of the gantry control circuitry 25, the high voltage generator 37 generates a high voltage to be applied to the X-ray tube 17 from power supplied from the power supply unit of the gantry 11 via the annular electrode. The high voltage generator 37 and the X-ray tube 17 are connected via a high voltage cable. The high voltage generated by the high voltage generator 37 is applied to the X-ray tube 17 via the high voltage cable.

The X-ray detector 19 detects the X-rays generated by the X-ray tube 17 and transmitted through the subject S. The X-ray detector 19 includes a plurality of X-ray detection elements arranged on a two-dimensional curved surface. Each X-ray detection element detects the X-rays from the X-ray tube 17 and converts them into an electrical signal having a peak value according to the intensity of the detected X-rays. Each X-ray detection element includes, for example, a scintillator and a photoelectric converter. The scintillator generates fluorescence upon receiving X-rays. The photoelectric converter converts the generated fluorescence into a charge pulse. The charge pulse has a peak value according to the intensity of the X-rays. More specifically, a device such as a photomultiplier or a photodiode, which converts photons into an electrical signal, is used as the photoelectric converter. Note that the X-ray detector 19 according to this embodiment is not limited to a detector of an indirect type that temporarily converts X-rays into fluorescence and then converts it into an electrical signal, and may be a detector of a direct type that directly converts X-rays into an electrical signal.

Data acquisition circuitry 39 acquires, for each view, digital data representing the intensity of the X-rays attenuated by the subject S. The data acquisition circuitry 39 is implemented by, for example, semiconductor integrated circuitry on which integration circuitry and an A/D converter provided in correspondence with each of the plurality of X-ray detection elements are implemented in parallel. The data acquisition circuitry 39 is connected to the X-ray detector 19 in the gantry 11. The integration circuitry integrates electrical signals from an X-ray detection element during a predetermined view period to generate an integrated signal. The A/D converter A/D-converts the generated integrated signal to generate digital data having a data value corresponding to the peak value of the integrated signal. The digital data after conversion is called raw data. Raw data is a set of digital values of X-ray intensity identified by the channel number and the column number of an X-ray detection element as the generation source and a view number representing an acquired view. The raw data is supplied to the console 50 via, for example, a noncontact data transmission unit stored in the gantry 11.

Note that the gantry 11 may store not only the X-ray tube 17, the X-ray detector 19, the rotation frame 21, the main frame, the power supply unit, the high voltage generator 37, and the data acquisition circuitry 39 described above but also various other units necessary for Ct imaging. For example, a cooling apparatus cools the X-ray tube may be attached to the rotation frame 21.

The gantry control circuitry 25 controls the high voltage generator 37, the rotation driving actuator 23, the column driving actuator 27, and the tilt driving actuator 29 under the control of system control circuitry 61 in the console 50. The gantry control circuitry 25 includes, as hardware resources, a predetermined processor such as a CPU or an MPU and a predetermined memory such as a ROM or a RAM. The gantry control circuitry 25 may be implemented by an ASIC, an FPGA, a CPLD, an SPLD, or the like. The processor implements the function by reading out a program saved in the memory and executing it. Note that instead of saving the program in the memory, the program may directly be installed in circuitry of the processor. In this case, the processor implements the function by reading out the program installed in the circuitry and executing it.

The console 50 includes an image reconstruction circuitry 51, an image processing circuitry 53, a monitor 55, an input interface (IF) circuitry 57, main storage circuitry 59, and the system control circuitry 61 which are connected via a bus. Data communication between The image reconstruction circuitry 51, the image processing circuitry 53, the monitor 55, the input IF circuitry 57, the main storage circuitry 59, and the system control circuitry 61 is performed via the bus.

The image reconstruction circuitry 51 reconstructs a CT image concerning the subject S based on raw data from the console 50. More specifically, The image reconstruction circuitry 51 includes preprocessing circuitry 511, projection data storage circuitry 513, and reconstruction operation circuitry 515. The preprocessing circuitry 511 preprocesses raw data from the gantry apparatus 10. The preprocessing includes logarithmic transformation and various kinds of correction processing such as X-ray intensity correction and offset correction. The preprocessed raw data is called projection data. The projection data storage circuitry 513 is a storage unit that stores the projection data generated by the preprocessing circuitry 511, such as an HDD, an SSD, or an integrated circuitry storage unit. The reconstruction operation circuitry 515 generates a CT image that expresses the spatial distribution of CT values concerning the subject S based on the projection data. As the image reconstruction algorithm, an existing image reconstruction algorithm, for example, an analytic image reconstruction method such as FBP (Filtered Back Projection) or CBP (Convolution Back Projection) or a statistical image reconstruction method such as ML-EM (Maximum Likelihood Expectation Maximization) or OS-EM (Ordered Subset Expectation Maximization) is used.

The image reconstruction circuitry 51 includes, as hardware resources, a processing unit (processor) such as a CPU, an MPU, or a GPU (Graphics Processing Unit) and a storage unit (memory) such as a ROM or a RAM. The image reconstruction circuitry 51 may be implemented by an ASIC, an FPGA, a CPLD, an SPLD, or the like. The processing unit implements the functions of the preprocessing circuitry 511 and the reconstruction operation circuitry 515 by reading out a program saved in the storage unit and executing it. Note that instead of saving the program in the storage unit, the program may directly be installed in circuitry of the processing unit. In this case, the processing unit implements the functions of the preprocessing circuitry 511 and the reconstruction operation circuitry 515 by reading out the program installed in the circuitry and executing it. Alternatively, dedicated hardware circuitry functioning as the preprocessing circuitry 511 and dedicated hardware circuitry functioning as the reconstruction operation circuitry 515 may be implemented in the image reconstruction unit.

The image processing circuitry 53 performs various kinds of image processing for the CT image reconstructed by The image reconstruction circuitry 51. For example, if the CT image is volume data, The image processing circuitry 53 performs three-dimensional image processing such as volume rendering, surface volume rendering, image value projection processing, MPR (Multi-Planer Reconstruction) processing, and CPR (Curved MPR) processing for the CT image to generate a display image. The image processing circuitry 53 includes, as hardware resources, a predetermined processor such as a CPU, an MPU, or a GPU and a predetermined memory such as a ROM or a RAM. The image processing circuitry 53 may be implemented by an ASIC, an FPGA, a CPLD, an SPLD, or the like.

The monitor 55 displays various kinds of information such as a two-dimensional CT image and a display image. As The monitor 55, for example, a CRT display, a liquid crystal display, an organic EL display, an LED display, a plasma display, or another arbitrary display known in the technical field can appropriately be used.

The input IF circuitry 57 accepts various kinds of instructions or information input from the user. As the input IF circuitry 57, a keyboard, a mouse, or various kinds of switches, or the like can be used. Note that the input IF circuitry 57 may be provided on the console 50 or the gantry apparatus 10.

The main storage circuitry 59 stores various kinds of information. The main storage circuitry 59 includes an HDD (Hard Disc Drive), an SSD (Solid State Drive), or an integrated circuitry storage unit. The main storage circuitry 59 may be a driving actuator or the like reads/writes various kinds of information from/to a portable storage medium such as a CD-ROM drive, a DVD drive, or a flash memory. For example, the main storage circuitry 59 stores a control program and the like concerning X-ray computed tomography imaging according to this embodiment.

The system control circuitry 61 includes a processor and a memory as hardware resources. The system control circuitry 61 functions as the core of the X-ray computed tomography imaging apparatus according to this embodiment. More specifically, the system control circuitry 61 reads out a control program stored in the main storage circuitry 59, loads it onto the memory, and controls the units of the X-ray CT apparatus in accordance with the loaded control program.

Note that the image reconstruction circuitry 51, the image processing circuitry 53, and the system control circuitry 61 may be integrated on a single board in the console 50 or distributed to a plurality of boards.

Placement of the gantry 11 and the columns 13 of the X-ray CT apparatus according to this embodiment will be described here.

Figure 4:
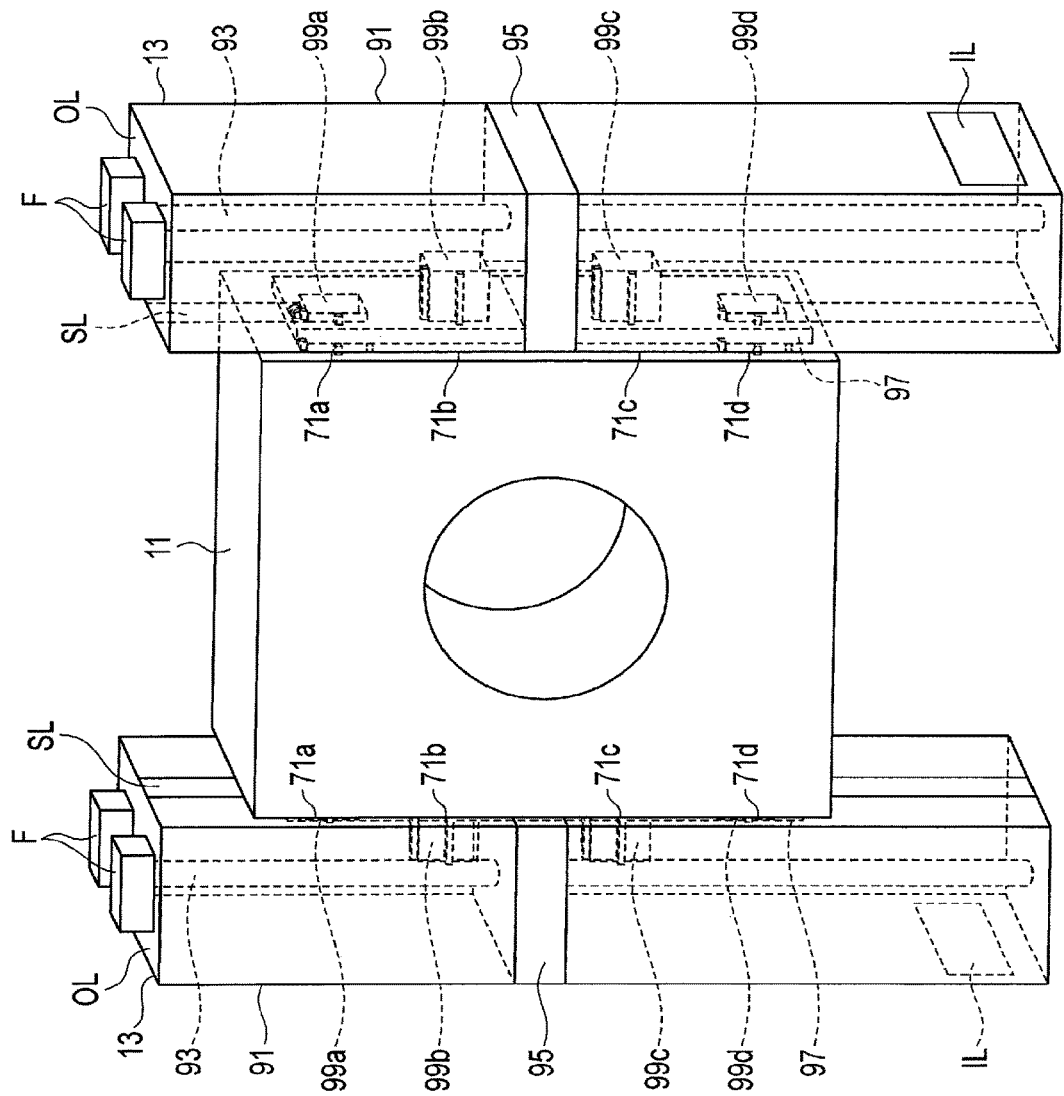
FIG. 4 is a view for explaining placement of the gantry and the columns shown in FIG. 1.

FIG. 4 is a view for explaining placement of the gantry 11 and the columns 13 shown in FIG. 1. As shown in FIG. 4, the gantry 11 is connected to the columns 13 via the bearings 77 and 96 so as to be rotatable about the tilt axis.

When CT-imaging the subject S in a second imaging mode (standing position imaging mode) in which CT imaging of the subject S in a standing or sitting position is performed, the gantry 11 is stationarily supported on the columns 13 to attain a state (first state) in which the center axis of the bore 15 of the gantry 11 is perpendicular to the floor surface of the examination room. For example, as shown in FIG. 4, the ducts 99b and 99c are inserted into the vent holes 71b and 71c to fit the gantry 11 between the columns 13. This makes it possible to stationarily support the gantry 11 on the columns 13 in a predetermined direction corresponding to the second imaging mode. In addition, an intake path from the intake port IL to the vent hole 71c of the gantry 11 and an exhaust path from the vent hole 71b of the gantry 11 to the exhaust port OL are formed.

When CT-imaging the subject S in a first imaging mode (lying position imaging mode) in which CT imaging of the subject S in a lying position is performed, the gantry 11 is stationarily supported on the columns 13 to attain a state (second state) in which the center axis of the bore 15 of the gantry 11 is parallel to the floor surface of the examination room. For example, as shown in FIG. 4, the ducts 99a and 99d are inserted into the vent holes 71a and 71d to fit the gantry 11 between the columns 13. This makes it possible to stationarily support the gantry 11 on the columns 13 in a predetermined direction corresponding to the first imaging mode. In addition, an intake path from the intake port IL to the vent hole 71d of the gantry 11 and an exhaust path from the vent hole 71a of the gantry 11 to the exhaust port OL are formed.

Figure 5:
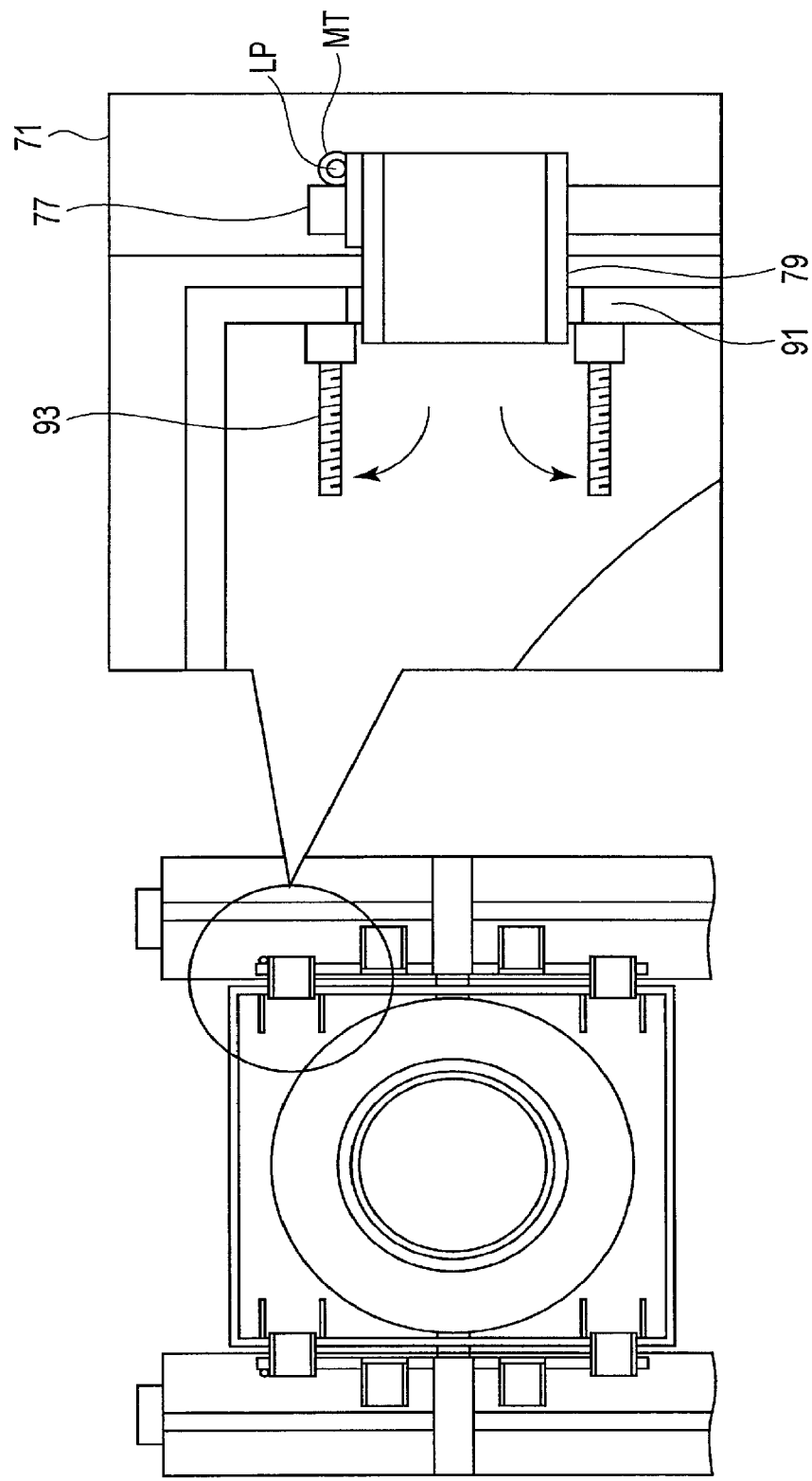
FIG. 5 is a view for explaining opening/closing of lids shown in FIG. 2B.

FIG. 5 is a view for explaining opening/closing of the lids 73 shown in FIG. 2B. As shown in FIG. 5, when fitting the gantry 11 between the columns 13, the duct driving actuators make the ducts 99a, 99b, 99c, and 99d project from the column housings 91. The projecting ducts 99a, 99b, 99c, and 99d push the lids 73. The lids 73 thus open. When canceling the fitting state between the gantry 11 and the columns 13, the duct driving actuators return the ducts 99a, 99b, 99c, and 99d into the column housings 91. The lids 73 pushed by the projecting ducts 99a, 99b, 99c, and 99d thus close.

An example of the operation of the X-ray CT apparatus according to this embodiment will be described here in detail with reference to the drawings.

(Switching Operation from First Imaging Mode to Second Imaging Mode)

FIG. 6 is a flowchart showing the procedure of a switching operation from the first imaging mode to the second imaging mode in the X-ray CT apparatus according to this embodiment. FIGS. 7A to 7D are views for explaining the procedure of the switching operation from the first imaging mode to the second imaging mode in the X-ray CT apparatus according to this embodiment. Note that as shown in FIG. 7A, the gantry 11 is supported by the columns 13 in a state capable of executing lying position imaging.

The imaging mode is switched from the first imaging mode to the second imaging mode by an operation of the operator (step S11). For example, the operator refers to a mode switching screen or the like displayed on the monitor 55 and selects the second imaging mode by the input IF circuitry 57, thereby switching the imaging mode from the first imaging mode to the second imaging mode. Note that the mode selection method is not limited to the above-described method. For example, the second imaging mode may be selected by a button or the like provided on the input IF circuitry 57.

After the second imaging mode is selected, the system control circuitry 61 transmits a first instruction signal to the gantry control circuitry 25 to execute driving control corresponding to the second imaging mode. Upon receiving the first instruction signal, the gantry control circuitry 25 controls driving of the motor MT of each duct driving actuator. The fitting state between the gantry 11 and the columns 13 via the ducts is thus canceled (step S13). For example, as shown in FIG. 7B, the duct 99a is removed from the vent hole 71a. In addition, the duct 99d is removed from the vent hole 71d. The fitting state between the gantry 11 and the columns 13 is thus canceled.

After the fitting state between the gantry 11 and the columns 13 is canceled, the gantry control circuitry 25 rotates the gantry 11 about the tilt axis by driving control of the tilt driving actuator 29 (step S15). For example, as shown in FIG. 7C, to enable execution of standing or sitting position imaging, the gantry 11 is rotated to a corresponding predetermined rotation angle. More specifically, the gantry 11 is rotated by 90° from the direction of the bore 15 of the gantry 11 shown in FIG. 7B.

After the gantry 11 is rotated, the gantry control circuitry 25 controls driving of the motor MT of each duct driving actuator. The gantry 11 is thus fitted between the columns 13 via the ducts (step S17). For example, as shown in FIG. 7D, the duct 99b is inserted into the vent hole 71b. In addition, the duct 99c is inserted into the vent hole 71c. The gantry 11 is thus fitted between the columns 13.

With the above-described operation, the switching operation from the first imaging mode to the second imaging mode is completed.

(Switching Operation from Second Imaging Mode to First Imaging Mode)

Figure 8:
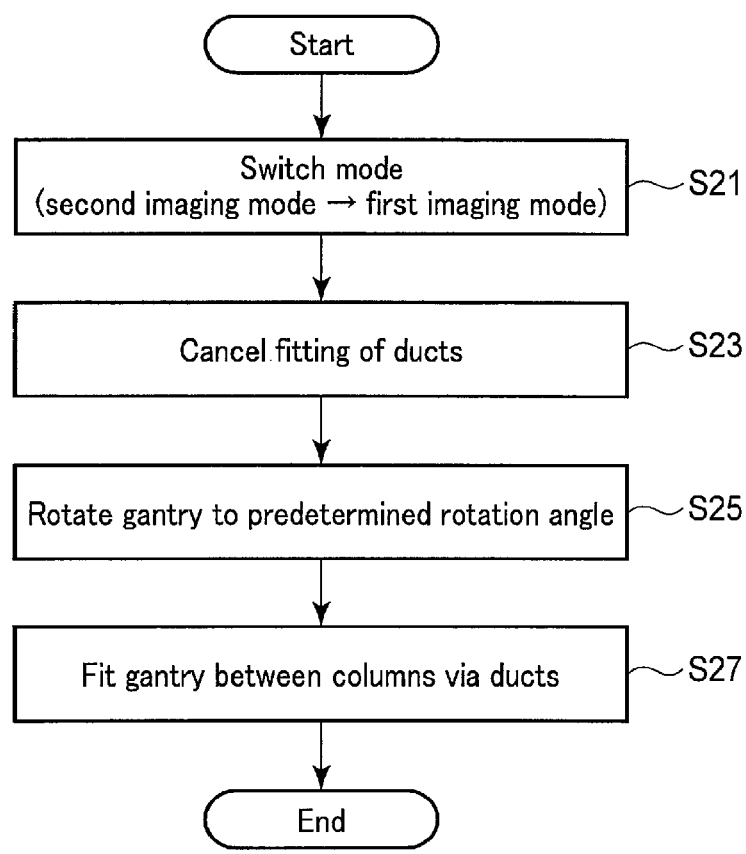
FIG. 8 is a flowchart showing the procedure of the switching operation from the second imaging mode to the first imaging mode in the X-ray CT apparatus according to the embodiment.
Figure 9A:
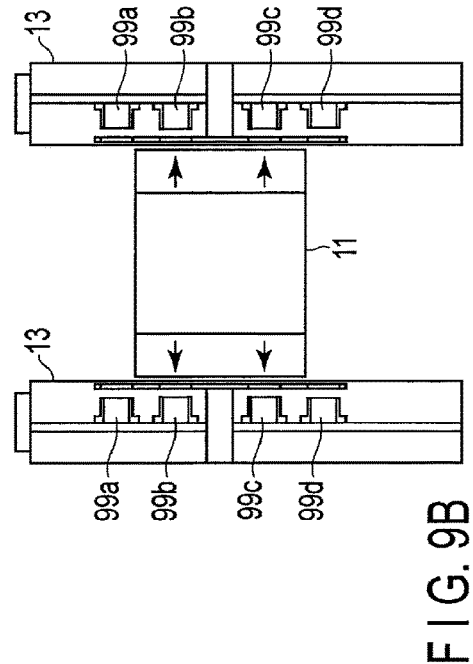
FIG. 9A is a view for explaining the procedure of the switching operation from the second imaging mode to the first imaging mode in the X-ray CT apparatus according to the embodiment.

FIG. 8 is a flowchart showing a switching operation from the second imaging mode to the first imaging mode in the X-ray CT apparatus according to this embodiment. FIGS. 9A to 9D are views for explaining the procedure of the switching operation from the second imaging mode to the first imaging mode in the X-ray CT apparatus according to this embodiment. Note that as shown in FIG. 9A, the gantry 11 is supported by the columns 13 in a state capable of executing standing or sitting position imaging.

The system control circuitry 61 switches the imaging mode from the second imaging mode to the first imaging mode by an operation of the operator (step S21). For example, the operator refers to a mode switching screen or the like displayed on the monitor 55 and selects the first imaging mode by the input IF circuitry 57, thereby switching the imaging mode from the second imaging mode to the first imaging mode. Note that the mode selection is not limited to the above-described method. For example, the first imaging mode may be selected by a button or the like provided on the input IF circuitry 57.

Figure 9B:
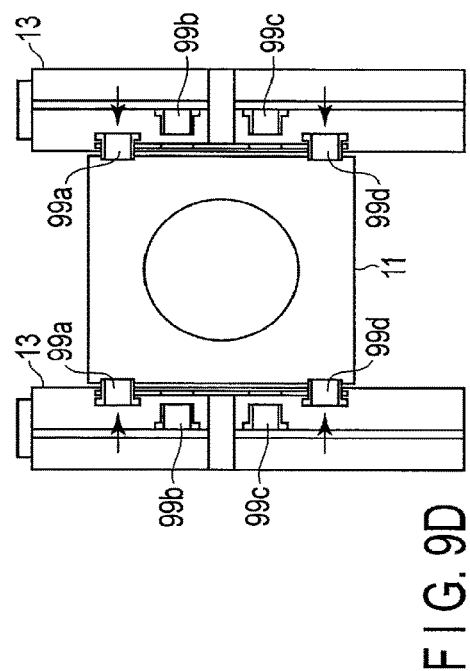
FIG. 9B is a view for explaining the procedure of the switching operation from the second imaging mode to the first imaging mode in the X-ray CT apparatus according to the embodiment.

After the first imaging mode is selected, the system control circuitry 61 transmits a second instruction signal to the gantry control circuitry 25 to execute driving control corresponding to the first imaging mode. Upon receiving the second instruction signal, the gantry control circuitry 25 controls driving of the motor MT of each duct driving actuator. The fitting state between the gantry 11 and the columns 13 via the ducts is thus canceled (step S23). For example, as shown in FIG. 9B, the duct 99b is removed from the vent hole 71b. In addition, the duct 99c is removed from the vent hole 71c. The fitting state between the gantry 11 and the columns 13 is thus canceled.

Figure 9C:
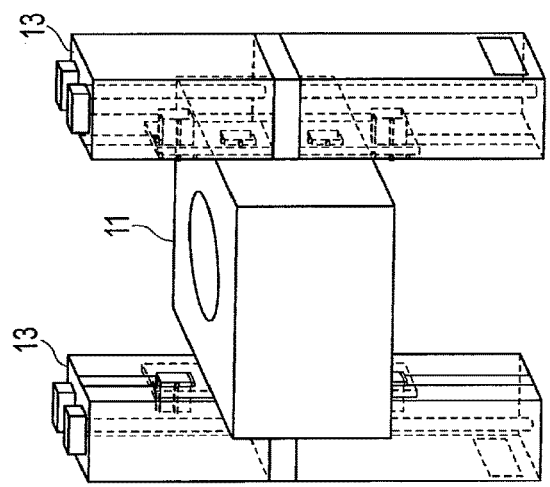
FIG. 9C is a view for explaining the procedure of the switching operation from the second imaging mode to the first imaging mode in the X-ray CT apparatus according to the embodiment.

After the fitting state between the gantry 11 and the columns 13 is canceled, the gantry control circuitry 25 rotates the gantry 11 about the tilt axis by driving control of the tilt driving actuator 29 (step S25). For example, as shown in FIG. 9C, to enable execution of lying position imaging, the gantry 11 is rotated to a corresponding predetermined rotation angle. More specifically, the gantry 11 is rotated by 90° from the direction of the bore 15 of the gantry 11 shown in FIG. 9B.

Figure 9D:
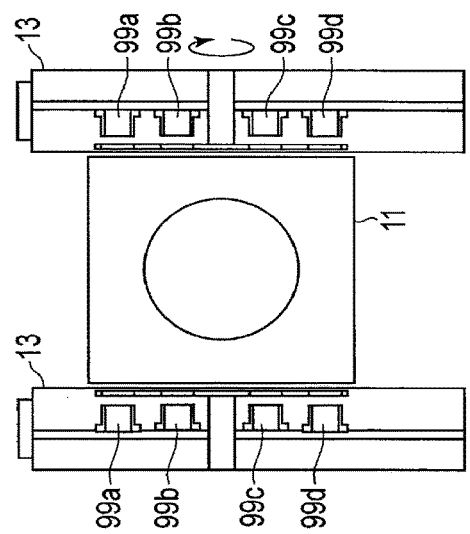
FIG. 9D is a view for explaining the procedure of the switching operation from the second imaging mode to the first imaging mode in the X-ray CT apparatus according to the embodiment.

After the gantry 11 is rotated, the gantry control circuitry 25 controls driving of the motor MT of each duct driving actuator. The gantry 11 is thus fitted between the columns 13 via the ducts (step S27). For example, as shown in FIG. 9D, the duct 99a is inserted into the vent hole 71a. In addition, the duct 99d is inserted into the vent hole 71d. The gantry 11 is thus fitted between the columns 13.

With the above-described operation, the switching operation from the second imaging mode to the first imaging mode is completed.

(Airflow Inside Gantry 11 and Columns 13 in First Imaging Mode)

FIG. 10 is a view showing a heat exhaust path in the X-ray CT apparatus according to the embodiment when executing lying position imaging.

As shown in FIG. 10, external air is drawn from the intake ports IL into the columns 13 ((1) in FIG. 10). The drawn air flows into the gantry 11 via the vent holes of the ducts 99d ((2) in FIG. 10). The air that has flowed into the gantry 11 via the vent holes of the ducts 99d rises inside the gantry 11 ((3) in FIG. 10). The air that has cooled the components provided in the gantry 11 flows into the columns 13 again via the vent holes of the ducts 99a ((4) in FIG. 10). The air that has flowed into the columns 13 again via the vent holes of the ducts 99a is exhausted from the exhaust ports OL to the outside ((5) in FIG. 10).

With the above-described airflow, the components provided in the gantry 11 are cooled by the air flowing from the columns 13 in the first imaging mode.

(Airflow Inside Gantry 11 and Columns 13 in Second Imaging Mode)

FIG. 11 is a view showing a heat exhaust path in the X-ray CT apparatus according to the embodiment when executing standing or sitting position imaging.

As shown in FIG. 11, external air is drawn from the intake ports IL into the columns 13 ((1) in FIG. 11). The drawn air flows into the gantry 11 via the vent holes of the ducts 99c ((2) in FIG. 11). The air that has flowed into the gantry 11 via the vent holes of the ducts 99c rises inside the gantry 11 ((3) in FIG. 11). The air that has cooled the components provided in the gantry 11 flows into the columns 13 again via the vent holes of the ducts 99b ((4) in FIG. 11). The air that has flowed into the columns 13 again via the vent holes of the ducts 99b is exhausted from the exhaust ports OL to the outside ((5) in FIG. 11).

With the above-described airflow, the components provided in the gantry 11 are cooled by the air flowing from the columns 13 in the second imaging mode.

According to the above-described arrangement, the following effects can be obtained.

The X-ray CT apparatus according to this embodiment includes the X-ray tube 17 generates X-rays, the X-ray detector 19 detects the X-rays, the gantry 11 including a bore 15 that forms a field of view and including the X-ray tube 17 and the X-ray detector 19 which are arranged to face each other across the bore 15, and the column 13 supports the gantry 11. The gantry 11 includes the vent hole 71c or 71d draws air into the gantry 11 and the vent hole 71a or 71b exhausts air from the gantry 11. The column 13 includes the intake port IL draws external air into the gantry 11, the vent hole of the duct 99c or the vent hole of the duct 99d, which communicates with the vent hole 71c or 71d, the vent hole of the duct 99a or the vent hole of the duct 99b, which communicates with the vent hole 71a or 71b, and the exhaust port OL exhausts internal air out of the column 13.

In the first imaging mode, the gantry 11 is fitted between the columns 13 via the ducts 99a and 99d, and air drawing and exhaust are performed as shown in FIG. 10. In the second imaging mode, the gantry 11 is fitted between the columns 13 via the ducts 99b and 99c, and air drawing and exhaust are performed as shown in FIG. 11.

With the above-described arrangement, the X-ray CT apparatus according to this embodiment can select an optimum heat exhaust path in each of the first imaging mode to execute lying position imaging and the second imaging mode to execute standing and sitting position imaging using the driven-type ducts 99a, 99b, 99c, and 99d driven by the duct driving actuators. It is therefore possible to select an optimum heat exhaust efficiency in both the first imaging mode and the second imaging mode.

Considering the airflow, the intake port IL is provided in the lower portion of the column 13, and the exhaust port OL is provided in the upper portion of the column 13. Air drawing and exhaust can be performed not only optimally but also at positions apart from the patient and the operator. It is therefore possible to reduce unpleasantness to the subject S and the operator.

When the gantry 11 is fitted between the columns via the ducts 99a, 99b, 99c, and 99d, a back-and-forth vibration generated during X-ray computed tomography imaging by the gantry apparatus 10 can be suppressed. That is, since an artifact caused by the back-and-forth vibration can be reduced, the quality of an X-ray CT image can be improved.

It is therefore possible to provide an X-ray computed tomography imaging apparatus and a gantry apparatus, which can reduce adverse effects generated in an X-ray CT apparatus used for both lying position imaging and at least one of standing position imaging or sitting position imaging.

Each of the vent holes 71a, 71b, 71c, and 71d provided in the gantry 11 and the ducts 99a, 99b, 99c, and 99d may be divided into a plurality of vent holes.

In the above-described embodiment, the ducts 99a, 99b, 99c, and 99d are provided in the columns 13 and inserted into the vent holes 71a, 71b, 71c, and 71d of the gantry 11. However, the embodiment is not limited to this. In this embodiment, the ducts may be placed in the gantry 11 and inserted into the vent holes provided in the columns 13. Alternatively, the ducts may be placed in both the gantry 11 and the columns.

In the above-described embodiment, the ducts 99a, 99b, 99c, and 99d of the columns 13 are inserted into the vent holes 71a, 71b, 71c, and 71d of the gantry 11, thereby forming the intake path and the exhaust path. However, the embodiment is not limited to this. In this embodiment, vent holes corresponding to the vent holes 71a, 71b, 71c, and 71d of the gantry 11 may be provided in the columns 13 without providing the ducts 99a, 99b, 99c, and 99d. In addition, the vent holes of the columns 13 corresponding to the vent holes 71a, 71b, 71c, and 71d of the gantry 11 may be made communicable with the vent holes 71a, 71b, 71c, and 71d of the gantry 11 using a predetermined method. For example, the gantry 11 and the columns 13 are brought into contact to communicate the vent holes 71a, 71b, 71c, and 71d of the gantry 11 with the vent holes of the columns 13 corresponding to the vent holes 71a, 71b, 71c, and 71d of the gantry 11. The intake path and the exhaust path may thus be formed.

Note that in this embodiment, the intake port IL is provided in the lower portion of the column 13, and the exhaust port is provided in the upper portion of the column 13. However, the embodiment is not limited to this. In this embodiment, the columns 13 may be constructed integrally with the CT room to draw air from below the floor and exhaust the air to the ceiling cavity.

The term "processor" used in the above explanation means, for example, a CPU (Central Processing Unit), a MPU (Micro Processing Unit), a GPU (Graphics Processing Unit), an ASIC (Application Specific Integrated Circuit), a programmable logic device (for example, an SPLD (Simple Programmable Logic Device), a CPLD (Complex Programmable Logic Device), or an FPGA (Field Programmable Gate Array), or the like. The processor implements a function by reading out a program saved in storage circuitry and executing it. Note that instead of saving the program in the storage circuitry, the program may directly be installed in circuitry of the processor. In this case, the processor implements the function by reading out the program installed in the circuitry and executing it. Note that each constituent element (each processing circuitry) of the embodiment may be implemented not by a single processor but by a plurality of processors. In addition, a plurality of constituent elements (a plurality of processing circuitry) may be implemented by a single processor.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X ray computed tomography imaging apparatus, comprising:
    a gantry configured to hold an X ray source configured to generate X rays and an X ray detector configured to detect the X rays; and
    a column configured to support the gantry in a first state in which a center axis of a bore of the gantry is perpendicular to a floor surface of an examination room and in a second state in which the center axis of the bore is parallel to the floor surface of the examination room,
    wherein the gantry comprises:
        a first gantry intake port configured to draw air in the first state; and
        a second gantry intake port configured to draw air in the second state, and
    the column comprises:
        a first column exhaust port configured to communicate with the first gantry intake port in the first state; and
        a second column exhaust port configured to communicate with the second gantry intake port in the second state.

2. The apparatus according to claim 1, wherein the column comprises:
    a first intake actuator configured to make the first gantry intake port communicate with the first column exhaust port in the first state; and
    a second intake actuator configured to make the second gantry intake port communicate with the second column exhaust port in the second state.

3. The apparatus according to claim 2, wherein the first intake actuator comprises:
    a first intake duct configured to make the first gantry intake port communicate with the first column exhaust port; and
    a first intake duct support actuator configured to insert the first intake duct from the first column exhaust port into the first gantry intake port, and
    the second intake actuator comprises:
        a second intake duct configured to make the second gantry intake port communicate with the second column exhaust port; and
        a second intake duct support actuator configured to insert the second intake duct from the second column exhaust port into the second gantry intake port.

4. The apparatus according to claim 3, further comprising:
    a first driving actuator configured to drive the first intake duct support actuator and the second intake duct support actuator, and
    first control circuitry configured to control the first driving actuator.

5. The apparatus according to claim 3, wherein the column fits the first column exhaust port in the first gantry intake port via the first intake duct, thereby stationarily supporting the gantry in the first state, and fits the second column exhaust port in the second gantry intake port via the second intake duct, thereby stationarily supporting the gantry in the second state.

6. The apparatus according to claim 3, wherein the column comprises a slit configured to make the gantry movable in a vertical direction in communication by the first intake duct or in communication by the second intake duct.

7. The apparatus according to claim 1, wherein the column comprises a column external intake port configured to draw external air to be drawn into the gantry.

8. The apparatus according to claim 7, wherein the column comprises an intake fan provided on the column external intake port and configured to draw the external air into the column.

9. The apparatus according to claim 7, wherein the column comprises an external intake duct configured to make the column external intake port communicate with at least one of the first column exhaust port and the second column exhaust port.

10. An X ray computed tomography imaging apparatus, comprising:
a gantry configured to hold an X ray source configured to generate X rays and an X ray detector configured to detect the X rays; and
a column configured to support the gantry in each of a first state in which a center axis of a bore of the gantry is perpendicular to a floor surface of an examination room and in a second state in which the center axis of the bore is parallel to the floor surface of the examination room,
wherein the gantry comprises:
a first gantry exhaust port configured to exhaust air from the gantry in the first state; and
a second gantry exhaust port configured to exhaust air from the gantry in the second state, and
the column comprises:
a first column intake port configured to communicate with the first gantry exhaust port in the first state; and
a second column intake port configured to communicate with the second gantry exhaust port in the second state.

11. The apparatus according to claim 10, wherein the column comprises:
a first exhaust actuator configured to make the first gantry exhaust port communicate with the first column intake port in the first state; and
a second exhaust actuator configured to make the second gantry exhaust port communicate with the second column intake port in the second state.

12. The apparatus according to claim 11, wherein the first exhaust actuator comprises:
a first exhaust duct configured to make the first gantry exhaust port communicate with the first column intake port; and
a first exhaust duct support actuator configured to insert the first exhaust duct from the first column intake port into the first gantry exhaust port, and
the second exhaust actuator comprises:
a second exhaust duct configured to make the second gantry exhaust port communicate with the second column intake port; and
a second exhaust duct support actuator configured to insert the second exhaust duct from the second column intake port into the second gantry exhaust port.

13. The apparatus according to claim 12, further comprising:
a second driving actuator configured to drive the first exhaust duct support actuator and the second exhaust duct support actuator; and
second control circuitry configured to control the second driving actuator.

14. The apparatus according to claim 12, wherein the column
fits the first column intake port in the first gantry exhaust port via the first exhaust duct, thereby stationarily supporting the gantry in the first state, and
fits the second column intake port in the second gantry exhaust port via the second exhaust duct, thereby stationarily supporting the gantry in the second state.

15. The apparatus according to claim 12, wherein the column comprises a slit configured to make the gantry movable in a vertical direction in communication by the first exhaust duct or in communication by the second exhaust duct.

16. The apparatus according to claim 10, wherein the column comprises a column external exhaust port configured to exhaust air in the gantry to outside.

17. The apparatus according to claim 16, wherein the column comprises an external exhaust fan provided on the column external exhaust port and configured to exhaust the air out of the column.

18. The apparatus according to claim 16, wherein the column comprises an external exhaust duct configured to make the column external exhaust port communicate with at least one of the first column intake port and the second column intake port.

19. A gantry apparatus, comprising:
a gantry configured to hold an X ray source configured to generate X rays and an X ray detector configured to detect the X rays; and
a column configured to support the gantry in a first state in which a center axis of a bore of the gantry is perpendicular to a floor surface of an examination room and in a second state in which the center axis of the bore is parallel to the floor surface of the examination room,
wherein the gantry comprises:
a first gantry intake port configured to draw air in the first state; and
a second gantry intake port configured to draw air in the second state, and
the column comprises:
a first column exhaust port configured to communicate with the first gantry intake port in the first state; and
a second column exhaust port configured to communicate with the second gantry intake port in the second state.

20. A gantry apparatus, comprising:
a gantry configured to hold an X ray source configured to generate X rays and an X ray detector configured to detect the X rays; and
a column configured to support the gantry in each of a first state in which a center axis of a bore of the gantry is perpendicular to a floor surface of an examination room and in a second state in which the center axis of the bore is parallel to the floor surface of the examination room,
wherein the gantry comprises:
a first gantry exhaust port configured to exhaust air from the gantry in the first state; and
a second gantry exhaust port configured to exhaust air from the gantry in the second state, and the column comprises:
- a first column intake port configured to communicate with the first gantry exhaust port in the first state; and
- a second column intake port configured to communicate with the second gantry exhaust port in the second state.

\* \* \* \* \*